US006943233B1

(12) United States Patent
Shoji

(10) Patent No.: US 6,943,233 B1
(45) Date of Patent: Sep. 13, 2005

(54) CYCLIC PEPTIDES AND AIDS VACCINES

(75) Inventor: Shozo Shoji, Kumamoto (JP)

(73) Assignee: Nissui Pharmaceutical Co., Ltd. (JP)

(*) Notice: Subject to any disclaimer, the term of this patent is extended or adjusted under 35 U.S.C. 154(b) by 0 days.

(21) Appl. No.: 10/110,853

(22) PCT Filed: Oct. 28, 1999

(86) PCT No.: PCT/JP99/05973

§ 371 (c)(1), (2), (4) Date: Apr. 17, 2002

(87) PCT Pub. No.: WO01/30509

PCT Pub. Date: May 3, 2001

(51) Int. Cl.[7] ................................................. C07K 5/00
(52) U.S. Cl. ................................ 530/300; 514/2; 514/9; 514/11; 930/10; 930/20; 930/220; 930/270; 530/350
(58) Field of Search ........................... 930/10, 20, 220, 930/270; 530/350, 300; 514/2, 9, 11

(56) References Cited

U.S. PATENT DOCUMENTS 5,229,490 A    7/1993  Tam ........................... 530/324

FOREIGN PATENT DOCUMENTS

| WO | WO9745543   | 4/1997  |
|----|-------------|---------|
| WO | WO97/32019  | 9/1997  |
| WO | WO97/47318  | 12/1997 |
| WO | WO97/47319  | 12/1997 |
| WO | 00/47609    | 8/2000  |

OTHER PUBLICATIONS

Bende. et al. Update: Search for an AIDS vaccine. AIDS Read, 10(9), 2000, pp. 526–537.*
Beyrer. The HIV/AIDS vaccine research effort: An update. The Johns Hopkins University AIDS Service, The Hopkins HIV Report, vol. 15 (1), Jan. 2003, pp. 1–16.*
Feinberg et al. AIDS vaccine models: challenging challenge viruses. Nature Medicine, vol. 8 (3), Mar. 2002, pp. 207–210.*
Misumi et al. A novel cyclic peptide immunization strategy for preventing HIV–1/AIDS infection and progression. Journal of Biological Chemistry, vol. 278, No. 34, 2003, pp. 32335–32343.*
Klausner et al. The need for a global HIV vaccine enterprise. Science, vol. 300, Jun. 2003, pp. 2036–2039.*
Desrosiers. Prospects for an AIDS vaccine. Nature Medicine, vol. 10(3), Mar. 2004, pp. 221–223.*
Nabel. Challenges and opportunities of development of an AIDS vaccine. Nature, vol. 410, Apr. 2001, pp. 1002–1007.*
Lee. Chapter 32 AIDS Vaccines: 32.1 Acquired immunodeficiency disease vaccines: design and development. AIDS: Biology, Diagosis, Treatment, and Prevention, fourth edition, edited by DeVitat, Jr. et al., Lippincott–Raven, 1997, pp. 605–616.*
Dorang et al. Identification of CXCR4 Domains that Support Coreceptor and Chemokine Receptor Functions. Journal of Virology. 1999. vol. 73, No. 4, 2752–2761.
Reeves et al. The Second Extracellular Loop of CXCR4 is Involved in C04–Independent Entry of Human Immunodeficiency Virus Type 2. Journal of General Virology. 1998, vol. 79, 1793–1799.
Olson et al. Differential Inhibition of Human Immunodeficiency Virus Type 1 Fusion, ge 120 Binding and CC–Chemokine Activity by monoclonal Antibodies to CCAS. Journal of Virology, 1999, vol. 73, No. 5, 4145–4155.
Dictionary of Immunology, Tokyo Kagaku Gojin K.K. 1993, p. 319.
HIV–1 Entry Cofactor: Functional cDNA Cloning of a Seven–Transmembrane, G Protein–Coupled Receptor. Yu Feng et al. Science, vol. 272, pp 872–877. May 10, 1996.
Homozygous Defect in HIV–1 Coreceptor Accounts for Resistance of Some Multiply–Exposed Individuals to HIV–1 Infection. Rong Liu et al. Cell, vol. 86, pp. 367–377. Aug. 9, 1996.
Ido et al, Dec. 12–13, 1998, 15th Meeting of the Japan Pharmacology Academy, Chemical Synthesis of a cyclo–oligo peptide and its biological activity.

* cited by examiner

Primary Examiner—James Housel
Assistant Examiner—Emily M. Le
(74) Attorney, Agent, or Firm—Lorusso & Loud

(57) ABSTRACT

Cyclic peptides which comprise, as a constituent chain or chains thereof, one or two amino acid sequences selected from the amino acid sequence Asn-Val-Ser-Glu-Ala-Asp-Asp-Arg-Tyr-Ile and the amino acid sequence Arg-Ser-Gln-Lys-Glu-Gly-Leu-His-Tyr-Thr, and AIDS vaccines containing at least one of the cyclic peptides as an active ingredient. From the in vivo absorption and antibody expression viewpoint, a substituent group is preferably bound to at least one active group selected from among the carboxyl, amino and hydroxyl groups contained in the cyclic peptides. The cyclic peptides can neutralize the second receptors which the HIV-1 virus utiliizes in the infection of humans therewith.

3 Claims, 6 Drawing Sheets

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 1

Arg Asp Asp Ala Glu Gly Glu Lys Gln Ser Asp Gly
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 2

Ile Tyr Arg Asp Asp Ala Glu Ser Val Asn Asp Gly
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 3

Thr Tyr His Leu Gly Glu Lys Gln Ser Arg Asp Gly
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Val Ser Glu Ala Asp Asp Arg Tyr Ile
 1               5                  10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Gln Lys Glu Gly Leu His Tyr Thr
 1               5                  10

<210> SEQ ID NO 6
<211> LENGTH: 5
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 6

Glu Ala Asp Asp Arg
 1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Gln Lys Glu Gly
 1               5
```

CYCLIC PEPTIDES AND AIDS VACCINES

TECHNICAL FIELD

The present invention relates to cyclic peptides and AIDS vaccines effective in preventing HIV-1 virus infection in human. More particularly, it relates to cyclic peptides which serve as antigens for producing a neutralizing antibody capable of neutralizing HIV-1 virus infection via the second receptors called CXCR4 and CCR5 and to AIDS vaccines which comprise the above antigens as active ingredients.

BACKGROUND ART

Second receptors which the pathogenic virus causative of AIDS (HIV-1 virus) utilized in infecting human were identified in 1996 (Yu Feng et al., Science, 272, 872–877, 1996). These receptors are two receptors called CXCR4 and CCR5 among the chemokine receptors already reported. It has been revealed that the HIV-1 virus utilizes one of the receptors for adsorption onto and entry into human lymphocytes, macrophages and dendritic cells to achieve infection.

On the other hand, about 1 to 2% of Caucasians reportedly have resistance to HIV-1 virus infection and it has been revealed that this is due to a genetic defect or genetic incompleteness of the second receptors (CXCR4 and CCR5), which are chemokine receptors (Hong Liu, et al., 86, 367–377, 1996).

These findings have called researchers' attention to the importance of neutralization of the second receptors in the prevention of HIV-1 virus infection and, in recent years, attempts have been made to produce a neutralizing antibody capable of neutralizing the second receptors. There is no report, however, about the successful creation of such a neutralizing antibody.

Accordingly, it is an object of the present invention to provide three-dimensional antigens capable of producing, in vivo, a neutralizing antibody capable of neutralizing the second receptors from the three-dimensional viewpoint by paying attention to the loop structures of the second receptor proteins without employing the conventional techniques of interpreting the peptides constituting the second receptors two-dimensionally. Another object is to provide AIDS vaccines which comprise such antigens as active ingredients.

DISCLOSURE OF INVENTION

The present inventors constructed a model of the second receptor in T cells (abbr.: CXCR4) and a model of the second receptor in macrophages (abbr.: CCR5) and observed them from the three-dimensional viewpoint. As a result, they explored the applicability of two peptides constituting the second subloop (UPL) in the respective second receptor protein molecules, namely T cell-derived $Asn_{176}$-$Val_{177}$-$Ser_{178}$-$Glu_{179}$-$Ala_{180}$-$Asp_{181}$-$Asp_{182}$-$Arg_{183}$-$Tyr_{184}$-$Ile_{185}$ (SEQ ID NO: 4) and macrophage-derived $Arg_{168}$-$Ser_{169}$-$Gln_{170}$-$Lys_{171}$-$Glu_{172}$-$Gly_{173}$-$Leu_{174}$-$His_{175}$-$Tyr_{176}$-$Thr_{177}$ (SEQ ID NO: 5), as constituent elements of a novel antigen for producing an HIV-1 virus infection-preventing antibody capable of neutralizing the second receptors and, as a result, they have now completed the present invention.

Thus, the present invention consists in a cyclic peptide which is a novel compound and comprises, as a constituent chain thereof, one or two amino acid sequences selected from among the amino acid sequence Asn-Val-Ser-Glu-Ala-Asp-Asp-Arg-Tyr-Ile (SEQ ID NO: 4) and the amino acid sequence Arg-Ser-Gln-Lys-Glu-Gly-Leu-His-Tyr-Thr (SEQ ID NO: 5) as well as in an AIDS vaccine comprising such compound as active ingredient.

Further, in a specific embodiment thereof, the present invention consists in a cyclic peptide which is a novel compound and represented by the formula (1) given below and in an AIDS vaccine comprising that compound as active ingredient.

Formula (1)

(SEQ ID NO: 2)

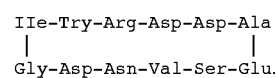

Further, in another specific embodiment, the present invention consists in a cyclic peptide which is a novel compound and represented by the formula (2) shown below and in an AIDS vaccine comprising that compound as active ingredient.

Formula (2)

(SEQ ID NO: 3)

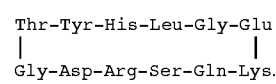

FIG. 1 shows the configuration of a T cell-derived second receptor protein molecule on the T cell membrane (FIG. 1, top left) and the configuration of a macrophage-derived second receptor molecule on the macrophage membrane (FIG. 1, top right), and a cyclic chimera dodecapeptide (abbr.: CXCR4-CCR5-CCDDP) (FIG. 1, bottom) represented by the formula (3) given below as synthesized from $Glu_{179}$-$Ala_{180}$-$Asp_{181}$-$Asp_{182}$-$Arg_{183}$ (SEQ ID NO: 6) (T cell-derived sequence) and $Ser_{169}$-$Gln_{170}$-$Lys_{171}$-$Glu_{172}$-$Gly_{173}$ (SEQ ID NO: 7) (macrophage-derived sequence) each occurring in the second subloop of each second receptor protein.

Formula (3)

(SEQ ID NO: 1)

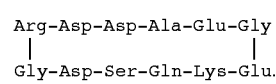

FIG. 2 shows the configuration of a T cell-derived second receptor protein molecule on the T cell membrane (FIG. 2, top) and a more specific CXCR4 cyclic dodecapeptide (SEQ ID NO: 2)(abbr.: CXCR4-UPL-CDDP) (FIG. 2, bottom) of the present invention as synthesized by using the same constituent chain peptide $Asn_{176}$-$Val_{177}$-$Ser_{178}$-$Glu_{179}$-$Ala_{180}$-$Asp_{181}$-$Asp_{182}$-$Arg_{183}$-$Tyr_{184}$-$Ile_{185}$ (SEQ ID NO: 4) as a part of the amino acid sequence of the second subloop (UPL) of the second receptor protein molecule.

FIG. 3 shows the configuration of a macrophage-derived second receptor protein molecule on the macrophage membrane (FIG. 3, top) and another more specific CCR5 cyclic dodecapeptide (SEQ ID NO: 3)(abbr.: CCR5-UPL-CDDP) (FIG. 3, bottom) of the present invention as synthesized by using the same constituent chain peptide $Arg_{168}$-$Ser_{169}$-$Gln_{170}$-$Lys_{171}$-$Glu_{172}$-$Gly_{173}$-$Leu_{174}$-$His_{175}$-$Tyr_{176}$-$Thr_{177}$ (SEQ ID NO: 5) as a part of the amino acid sequence of the second subloop (UPL) of the second receptor protein molecule.

Figure 1:
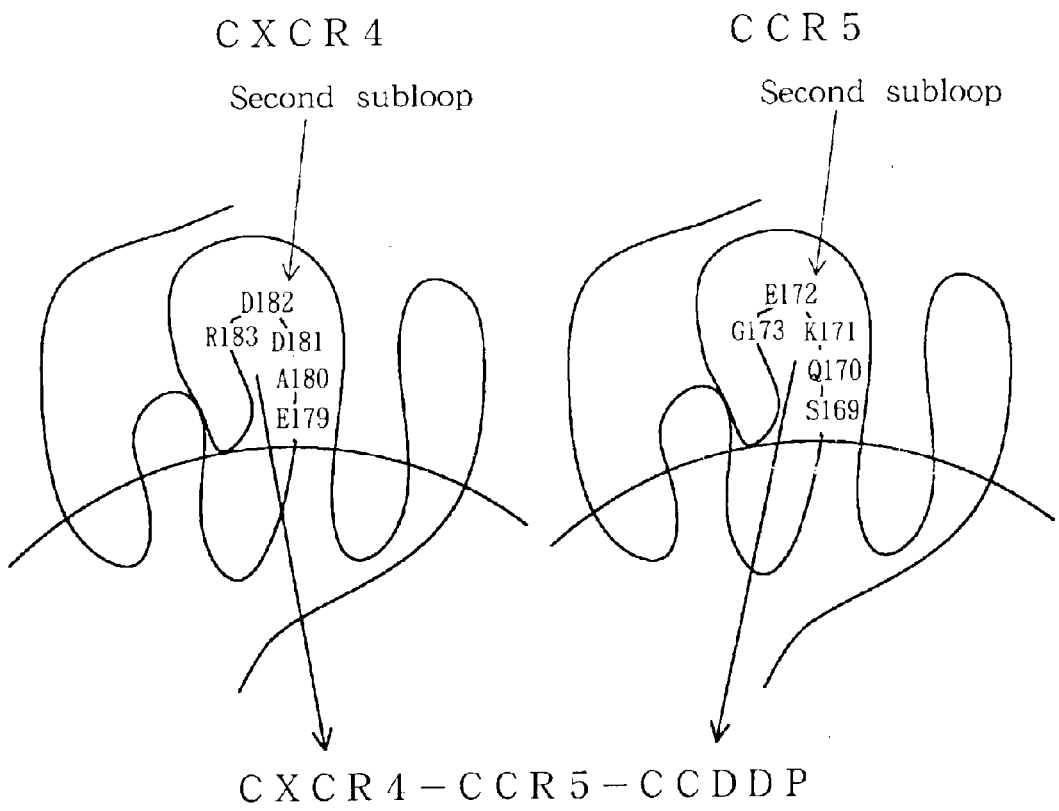
Figure 1:
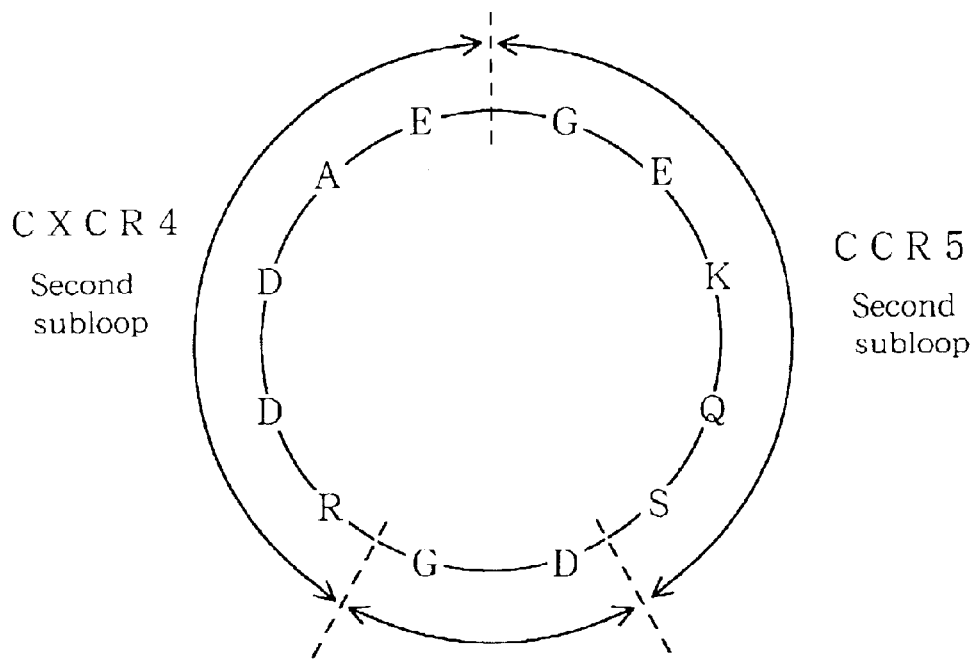

As shown in FIG. 1, the T cell-derived second receptor protein molecule (CXCR4) has a configuration comprising a first loop, a second loop, a third loop and a second subloop, and the macrophage-derived second receptor protein molecule (CCR5) also has a configuration comprising a first loop, a second loop, a third loop and a second subloop.

The second subloop in the T cell-derived second receptor protein molecule (CXCR4) contains the amino acid sequence $Gul_{179}$-$Ala_{180}$-$Asp_{181}$-$Asp_{182}$-$Arg_{183}$ (SEQ ID NO: 6) (FIG. 1, top left), and the second subloop in the macrophage-derived second receptor molecule (CCR5) contains the amino acid sequence $Ser_{169}$-$Gln_{170}$-$Lys_{171}$-$Glu_{172}$-$Gly_{173}$ (SEQ ID NO: 7) (FIG. 1, top right).

The cyclic chimera dodecapeptide (FIG. 1, bottom) represented by the above formula (3) is obtained by causing two peptides respectively having the amino acid sequences contained in both second subloops of CXCR4 and CCR5, namely $GU_{179}$-$Ala_{180}$-$Asp_{181}$-$Asp_{182}$-$Arg_{183}$ (SEQ ID NO: 6) contained in the T cell sequence and $Ser_{169}$-$Gln_{170}$-$Lys_{171}$-$Glu_{172}$-$Gly_{173}$ (SEQ ID NO: 7) contained in the macrophage sequence, to form a ring via Gly-Asp- as a spacer arm dipeptide.

Figure 2:
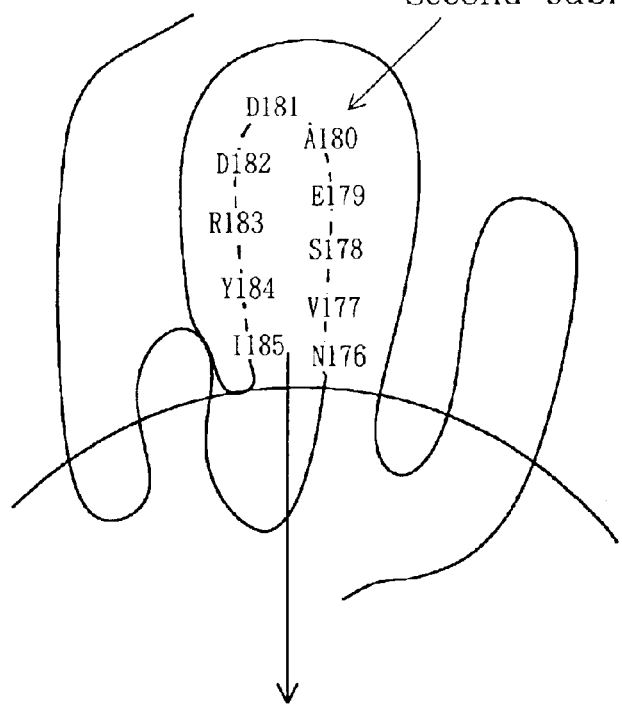
Figure 2:
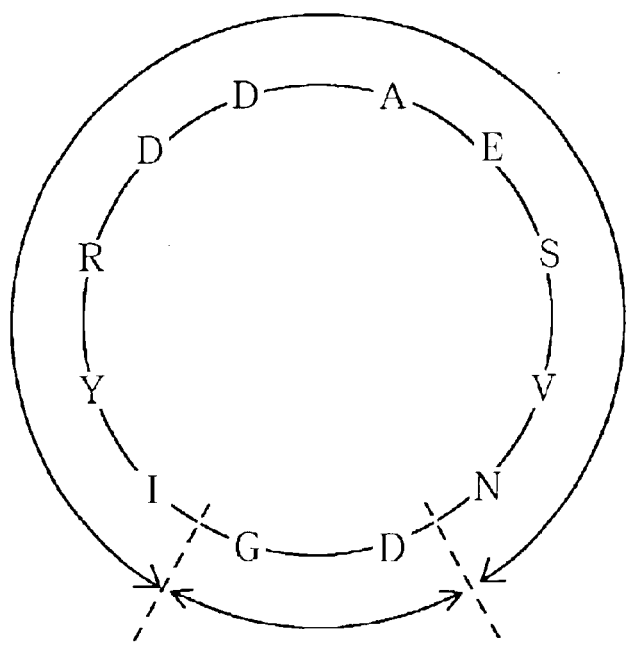

The novel compound cyclic dodecapeptide of the invention as represented by the above formula (1) (FIG. 2, bottom) is obtained by causing the amino acid sequence $Asn_{176}$-$Val_{177}$-$Ser_{178}$-$Glu_{179}$-$Ala_{180}$-$Asp_{181}$-$Asp_{182}$-$Arg_{183}$-$Tyr_{184}$-$Ile_{185}$ (SEQ ID NO: 4) contained in the second subloop (UPL) in the T cell-derived second receptor protein (CXCR4) to form a ring via Gly-Asp- as a spacer arm dipeptide.

Figure 3:
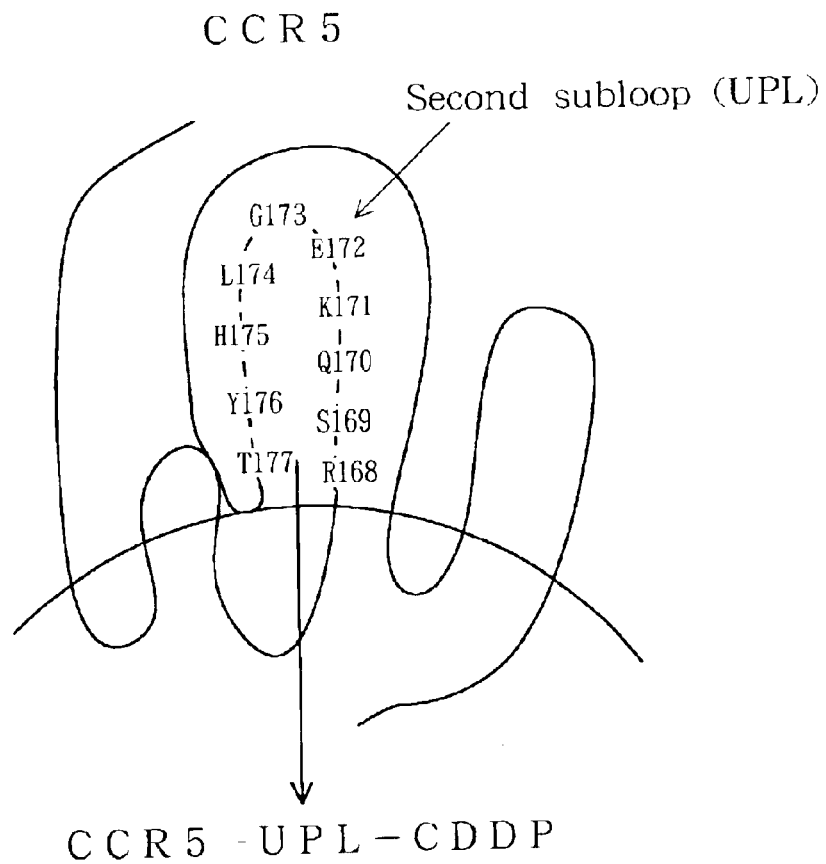
Figure 3:
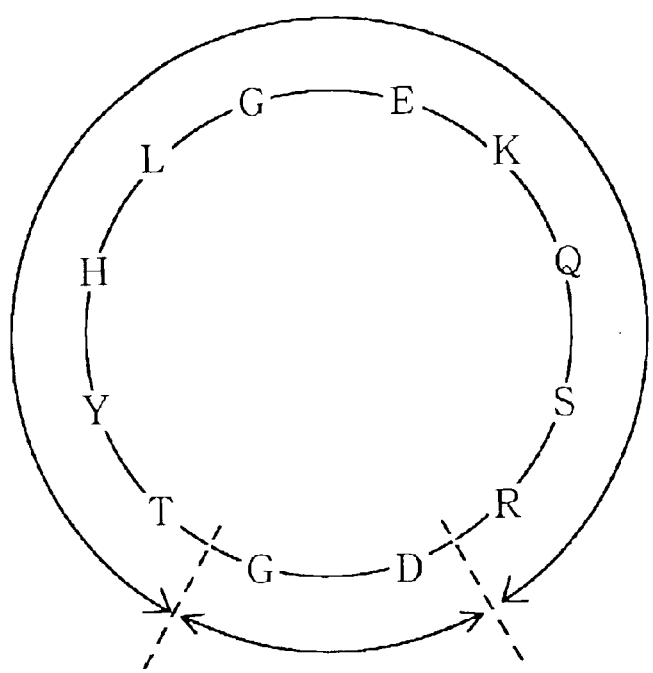

The novel compound cyclic dodecapeptide of the invention as represented by the above formula (2) (FIG. 3, bottom) is obtained by causing the amino acid sequence $Arg_{168}$-$Ser_{169}$-$Gln_{170}$-$Lys_{171}$-$Glu_{172}$-$Gly_{173}$-$Leu_{174}$-$His_{175}$-$Tyr_{176}$-$Thr_{177}$ (SEQ ID NO: 5) contained in the second subloop (UPL) in the macrophage-derived second receptor protein (CCR5) to form a ring via Gly-Asp- as a spacer arm dipeptide.

Preferably, an active group(s) selected from among the carboxyl, amino and hydroxyl groups contained in the cyclic dodecapeptide of the present invention as represented by the above formula (1) or (2) is (are) bonded to a substituent group so that the absorption into the living body and the antibody expression may be facilitated. Such a substituent can be selected from among:

the residue of a fatty acid $CH_3(CH_2)_n$—COOH (n: 0 to 20)

the residue of an alcohol $CH_3(CH_2)_n$—OH (n: 0 to 20) and unsaturated compound residues corresponding to such compound residues; these are preferred since they have bio-compatibility.

As appropriate examples of the fatty acid, there may be mentioned lauric acid, myristic acid, palmitic acid, stearic acid, arachidonic acid, and unsaturated fatty acids corresponding thereto. As appropriate higher alcohols, there may be mentioned lauryl alcohol, myristyl alcohol, palmityl alcohol, stearyl alcohol, eicosanol, and unsaturated alcohols corresponding to these.

The cyclic peptide of the invention as represented by the above formula (1) or (2) can be utilized as an immunogen for producing a second receptor-neutralizing antibody capable of inhibiting HIV-1 virus infection. In the following, mention is made of such immunogen.

An assaying antigen for antibody screening is prepared by binding the cyclic peptide of the invention to a solid phase resin. Separately, mice are immunized with an immunogen, for example, a cyclic dodecapeptide-multiple antigen peptide (abbr: CDDP-MAP), and monoclonal antibodies are prepared by the conventional hybridoma technique. As for the anti-infective activity against HIV-1 virus, several hybridomas (fused cells between antibody-producing B cells and myeloma cells (cancer cells)) are prepared by the above method and anti-HIV-1 virus activity assaying is carried out in the conventional manner using the hybridoma culture supernatants, whereby the culture supernatants are found to prevent HIV-1 virus infection.

Thus, the cyclic peptide of the present invention can be used as an immunogen for producing antibodies having inhibitory effects against HIV-1 virus infection and therefore is useful as an active ingredient in AIDS vaccines.

The AIDS vaccines according to the invention comprise the above-mentioned cyclic peptide as an active ingredient, and the active ingredient may be in a form modified by a substituent(s) and/or appendage(s) or may be in the form of a pharmacologically acceptable salt. The pharmacologically acceptable salt includes salts with hydrochloric acid, sulfuric acid, nitric acid, nitrous acid, hydrobromic acid, hydroiodic acid, phosphoric acid, and organic acids.

An example of the modification of the compound of the formula (1) which has a higher fatty acid moiety as a substituent is described below.

Formula (4)

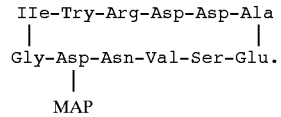

(SEQ ID NO: 2)

The above formula (4) is a result of binding of the cyclic dodecapeptide represented by the formula (1) to a MAP resin. 5 equivalents of 9-Fluorenylmethoxycarbonyldimethylsulfo nium methyl sulfate (Fmoc-DSP; tradename, product of Novabiochem) is added to 1 equivalent of the cyclic dodecapeptide-MAP of formula (4) to thereby block the ε-amino group of $K_4$ of the cyclic dodecapeptide-MAP and then the carboxyl groups ($E_5$, $E_7$) are activated with EDC, DCC, BOP or the like, and an excess of a higher alcohol [$CH_3(CH_2)_n$—OH] is added to thereby effect esterification. Alternatively, the hydroxyl group of Ser of the cyclic dodecapeptide-MAP of the formula (4) is esterified by the acid chloride [$CH_3(CH_2)_n$—COCl] method and, after elimination of Fmoc, the resulting ester is used as a base material of the peptide vaccine. When the vaccine is administered to the living body, it is delivered to lymphoid tissues, where the ester is hydrolyzed. The thus-regenerated original cyclic peptide-MAP represented by the formula (4) activates the immune system, whereby antibodies are produced and the AIDS virus infection is neutralized.

The AIDS vaccines according to the invention can be used in the form of pharmaceutical preparations for oral or non-oral administration. The oral dosage form includes tablets, powders, granules, capsules, microcapsules, solutions and the like. The non-oral or parenteral dosage form includes solutions, mainly injectable solutions, and suppositories, among others. Generally, these preparations may contain one or more of pharmaceutical preparation auxiliaries or additives well known in the art, for example carriers, excipients, binders, disintegrants, lubricants, stabilizers, and flavors.

The dose thereof may vary according to the symptom and/or age. In the case of oral administration, a daily dose of 0.1 to 1,000 mg/kg of body weight can be administered to ordinary adults.

BEST MODES FOR CARRYING OUT THE INVENTION

EXAMPLE 1

(1) Synthesis of a Cyclic Chimera Peptide Comprising Second Subloops of Two Types of Second Receptors for HIV-1

The resin used for solid phase synthesis of the peptide was a 2-chlorotrisyl chloride resin, which will not impair the protective groups on various amino acid residues and from which the peptide can be separated with a weak acid. A 0.25-mmol (368 mg) portion of the resin was weighed and used. The peptide synthesis was carried out according to the Fmoc (9-fluorenylmethoxycarbonyl) chemistry and an Fmoc-side chain-protected peptide-resin was obtained by starting the synthesis from the C terminus on a fully automated peptide synthesizer using the following Fmoc-side chain-protected amino acids 1) to 12) (1.0 mmol each).

| | | |
|---|---|---|
| 1) | Fmoc-Gly-OH | 1.0 mmol |
| 2) | Fmoc-L-Arg(Pmc)-OH | 1.0 mmol |
| 3) | Fmoc-L-Asp(OtBu)-OH | 1.0 mmol |
| 4) | Fmoc-L-Asp(OtBu)-OH | 1.0 mmol |
| 5) | Fmoc-L-Ala-OH | 1.0 mmol |
| 6) | Fmoc-L-Glu(OtBu)-OH | 1.0 mmol |
| 7) | Fmoc-Gly-OH | 1.0 mmol |
| 8) | Fmoc-L-Glu(OtBu)-OH | 1.0 mmol |
| 9) | Fmoc-L-Lys(Boc)-OH | 1.0 mmol |
| 10) | Fmoc-L-Gln(Trt)-OH | 1.0 mmol |
| 11) | Fmoc-L-Ser(tBu)-OH | 1.0 mmol |
| 12) | Fmoc-L-Asp(OBzl)-OH | 1.0 mmol |

The abbreviations used in identifying the above Fmoc-side chain-protected amino acids have the following meanings:
Pmc: 2,2,5,7,8-Pentamethylchroman-6-sulfonyl
OtBu: O-tert-butyl
Boc: Benzyloxycarbonyl
Trt: Trityl
tBu: tert-Butyl
OBzl: O-Benzyl 300 mg of the protected peptide resin obtained in the above process was admixed with 5 ml of an acetic acid/trifluoroethanol/dichloromethane (1:1:8) mixture, the resulting mixture was stirred at room temperature for 30 minutes and then filtered to thereby separate the side-chain protected peptide liberated with the weak acid from the resin, and ether was added to the filtrate in the conventional manner. To the thus-obtained precipitate was added an appropriate amount of acetonitrile, followed by lyophilization. By causing the carboxyl group of the C terminal Gly of this side chain-protected linear dodecapeptide to condense with the amino group of the amino terminal Asp(OBzl), a cyclic chimera dodecapeptide was synthesized as follows.

130 mg of the side chain-protected linear dodecapeptide was dissolved in 80 ml of a dimethylformamide solution containing 10% trifluoroethanol, 5 times the amount of the peptide of benzotriazole-1-yloxytris(dimethylamino) phosphonium hexafluorophosphate (abbr.: BOP) was added, and the mixture was allowed to stand at room temperature for 24 hours to thereby allow the reaction to proceed. The reaction was stopped by adding 1 to 2 ml of water, and the mixture was concentrated to 10 ml under reduced pressure with warming. About 40 ml of water was added, and the resulting precipitate was collected by centrifugation, washed with two 20-ml portions of water and lyophilized. Purification by the conventional method gave 80 mg of the side chain-protected cyclic chimera dodecapeptide.

This side chain-protected cyclic chimera dodecapeptide was dissolved in 10 ml of dimethylformamide, 50 mg of palladium-carbon was added, and catalytic reduction with hydrogen gas was carried out for 24 hours to thereby eliminate the protective group OBzl on the COOH group of the Asp residue in the spacer arm dipeptide. After concentration, water was added, and the resulting precipitate was washed twice with water and lyophilized to give the carboxymethyl side chain-protected cyclic chimera dodecapeptide (15 mg).

Figure 4:
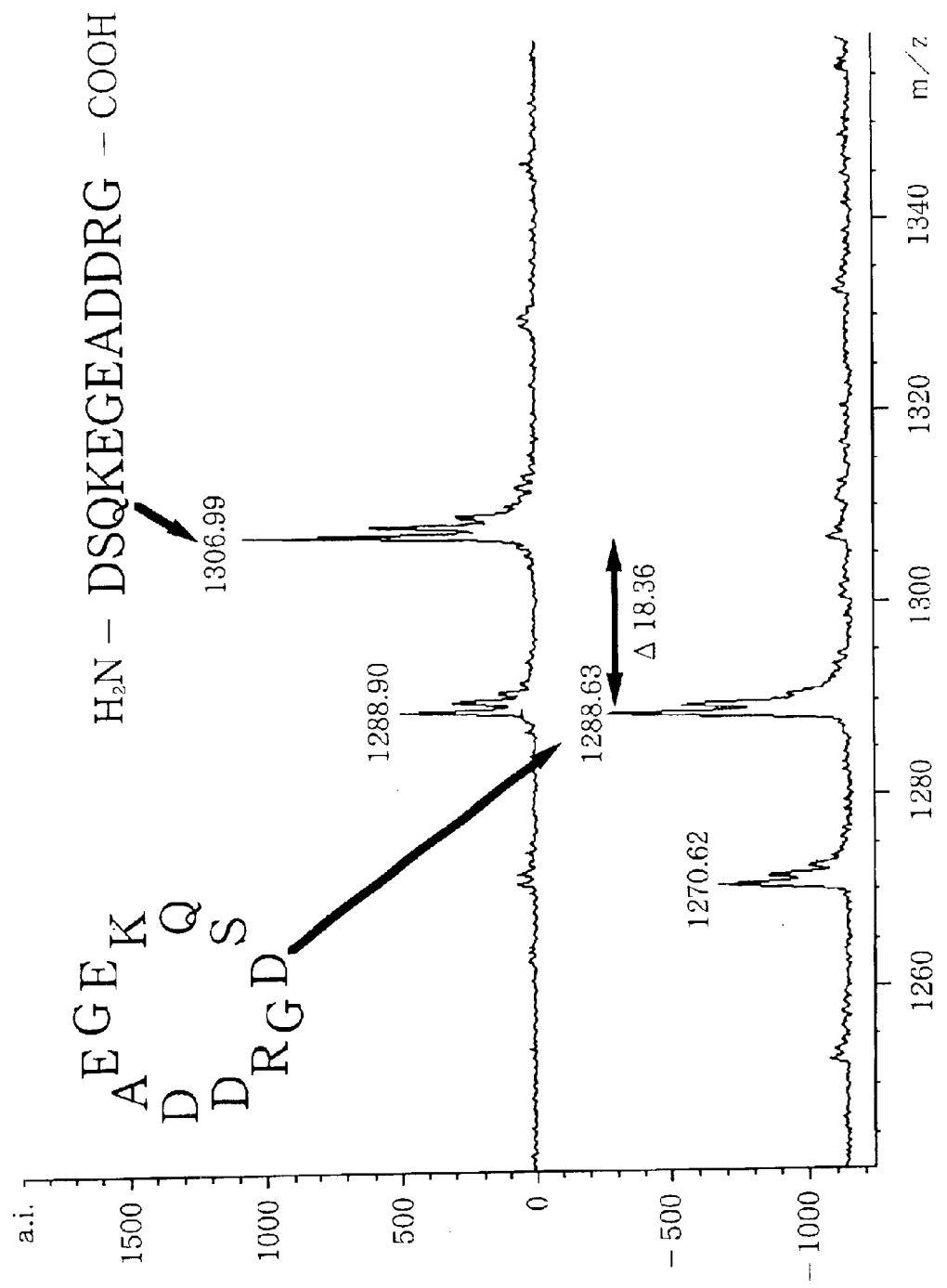
FIG. 4 shows the MALDI TOF mass spectra for the cyclic chimera dodecapeptide (CXCR4-CCR5-CCDDP) represented by the formula (3) (SEQ ID NO: 1) and the corresponding linear (noncyclic) peptide.

For identifying the cyclic chimera dodecapeptide, all the protective groups were eliminated in the conventional manner and laser mass spectrometry was performed (MALDI-TOF mass spectrometer). The theoretical values and the values measured in laser mass spectrometry for the cyclic peptide and linear (noncyclic) peptide are shown in Table 1 given later herein. The MALDI TOF mass spectra for the cyclic chimera dodecapeptide and linear (noncyclic) peptide are shown in FIG. 4. The cyclic chimera dodecapeptide represented by the formula (3) was thus identified based on the results shown (reduction by 18, namely the molecular mass of water, as a result of dehydration condensation under ring formation). The cyclic chimera dodecapeptide obtained in this Example 1 is sometimes referred to as CXCR4-CCR5 cyclic chimera dodecapeptide or CXCR4-CCR5-CCDDP or simply as CCDDP.

(2) Preparation of an Immunogen Comprising the Cyclic Chimera Dodecapeptide-MAP (abbr.: CCDDP-MAP)

The carboxyl group of the carboxymethyl side chain-blocked cyclic chimera dodecapeptide (abbr.: CM-SBCCDDP) was condensed with the amino group of tetra-branching polylysine of a MAP-resin by the BOP method, as follows.

70 mg (32 μmol) of the MAP-resin (0.46 mmol, of tetra-branching polylysine/resin) was swelled in dimethylformamide (abbr.: DMF), the MAP-resin was deprotected (elimination of Fmoc) with three 10-ml portions of 20% piperidine/DMF, washed with three 5-ml portions of isopropanol and then deprived of the isopropanol, to expose the amino terminus of the tetra-branching polylysine. To this MAP-resin was added 10 ml (32 mmol) of a solution of the carboxymethyl side chain-blocked cyclic dodecapeptide in dimethylformamide, and the binding between them was effected by the BOP method. The peptide was separated from the side chain-blocked cyclic chimera dodecapeptide (abbr.: SBCCDDP)-MAP-resin in the conventional by treatment with trifluoroacetic acid (abbr.: TFA), whereby 12 mg of the cyclic chimera dodecapeptide-MAP (abbr.: CCDDP-MAP) was obtained. This was used as an immunogen for preparing anti-cyclic chimera dodecapeptide (abbr.: CCDDP-MAP) monoclonal antibodies.

(3) Preparation of a CCDDP-PIN Resin (Crown Resin) as an Assaying Antigen for Preparing Anti-cyclic Chimera Dodecapeptide (anti-CCDDP) Monoclonal Antibodies The assaying antigen for efficiently producing anti-CCDDP monoclonal antibodies from culture supernatants was prepared in the following manner. The side chain-blocked cyclic dodecapeptide was bound to β-Ala at the pointed end of the PIN resin (crown resin) according to the epitope scanning kit manual (Chiron Mimotopes Pty Ltd, Clayton, Victoria, Australia) to give the corresponding CCDDP-PIN resin (crown resin).

(4) Preparation of Monoclonal Antibody-producing Hybridomas

Balb/c mice were primarily immunized using the cyclic chimera dodecapeptide-MAP as the immunogen peptide and cell fusion was carried out in the conventional manner using myeloma cells (P3U1) and polyethylene glycol. After fusion, selective culture was carried out using HAT medium and, for the wells in which hybridoma cells formed colonies, the antibody titer in each culture supernatant was determined by the multi-PIN ELISA method using the antigen peptide. For each cell group judged as antibody-positive, cloning was performed twice by limiting dilution and a monoclonal hybridoma line was established by the conventional method. For basal immunization, the lyophilized immunogen peptide was dissolved in PBS(−) to a concentration of 1 mg/ml and this solution was admixed, at a ratio of 1:1.2 to 1:1.4, with the immunostimulator Freund's complete adjuvant (FCA) or Freund's incomplete adjuvant (FIA), and the thus-prepared emulsion was used. This emulsion was intraperitoneally administered at a dose of 400 μl/mouse four times in total at one-week intervals. For the first two administrations, the emulsion with FCA was used and, for the last two administrations, the emulsion with FIA was used. The final or boost immunization was carried out after the lapse of one month following completion of the basal immunization by intravenous administration, through the tail vein, of 200 μg/ml solution of the lyophilized immunogen peptide (MAP) in PBS(−) at a dose of 200 μl/mouse.

1. Preparation of Splenic Cells and Cell Fusion

The preparation of splenic cells and cell fusion were carried out in the conventional manner. Three or four days after the final immunization, mice were sacrificed by exsanguinations, splenic cells were excised and loosened in Hank's balanced salt solution (HBSS) and erythrocytes were removed by hemolytic buffer treatment and centrifugation. The spienic cells thus prepared were mixed with P3U1 cells at a ratio of P3U1:splenic cells=1:8 to 1:10, and the mixture was centrifuged. A polyethylene glycol solution was added to the pellet obtained to thereby effect fusion. After fusion treatment, the fused cells were gently suspended in HAT medium, and the suspension was distributed in the wells of 48-well plates and cultured at 37° C. until the fused cells formed colonies.

2. Screening for Antibody-producing Hybridomas

The screening for antibody-producing hybridomas was effected and the desired hybridomas were selected by continuously carrying out primary screening by the ELISA method using the immunogen peptide as a solid phase antigen and secondary screening using the multi-PIN peptide as a solid phase antigen. In ELISA, the hybridoma culture supernatant was used as a primary antibody. peroxidase (POD)-labeled anti-mouse IgG as a secondary antibody. TMBZ (3,3',5,5'-tetramethyl-benzidine) as a color substrate, and 0.3 N $H_2SO_4$ as a color development stop solution, and the absorbances were measured at a dominant wavelength of 450 nm and at a reference wavelength of 630 nm.

3. Cloning of a Desired Antibody-producing Hybridoma Line

A monoclonal hybridoma strain showing a high antibody titer in the screening assay was subjected to limiting dilution to one cell/well. The thus-cloned cells were distributed, together with feeder cells prepared from the murine thymus, into the wells of 96-well plates and cultured. After two repetitions of this cloning procedure, the group of monoclonal cells obtained was subjected to screening by multi-PIN ELISA using the antigen peptide. The cell line which showed the highest antibody titer in both ELISA screenings was selected as the monoclonal antibody-producing hybridoma line, and the monoclonal antibody was purified from the culture supernatant thereof in the conventional manner. The subclass of this monoclonal antibody was IgM κ. This hybridoma was deposited on Feb. 3, 1999 with the Agency of Industrial Science and Technology National Institute of Life Science and Human Technology under the accession number FERM P-17198. This deposition is to be transferred as of Oct. 27, 1999 to the international deposition under the Budapest Treaty under the accession number PERM BP-6925. The cell line established was extended and, after cultivation, the cells were frozen stored in a liquid nitrogen tank.

(5) Anti-HIV Activity Assay

The anti-HIV activity was measured by the method of Maeda et al. (Y. Maeda, et al., 12th World AIDS Conference Geneva, Abstract P4, Jun. 28–Jul. 3, 1998). The culture fluid of the anti-CCDDP monoclonal antibody (hereinafter referred to also as CPMAb)-producing cells created by the present inventors and that of the corresponding non-antibody-producing cells as a control as obtained under the same conditions were used. The antibody-containing culture fluid (200 μl) reduced the rate of infection with HIV-1 virus to 61% in 30 minutes and to 35% in 60 minutes as compared with the control and it was thus established that it inhibits the infectivity of HIV-1 virus.

EXAMPLE 2

Synthesis of the CXCR4 Cyclic Dodecapeptide

A Fmoc-side chain protected peptide resin was obtained by starting the synthesis from the C terminus on a fully automated peptide synthesizer following the same procedure as in Example 1 using the following Fmoc-side chain-protected amino acids 1) to 12).

| 1) | Fmoc-Gly-OH | 1.0 mmol |
| 2) | Fmoc-L-Ile-OH | 1.0 mmol |
| 3) | Fmoc-L-Tyr(tBu)-OH | 1.0 mmol |
| 4) | Fmoc-L-Arg(Pmc)-OH | 1.0 mmol |
| 5) | Fmoc-L-Asp(OtBu)-OH | 1.0 mmol |
| 6) | Fmoc-L-Asp(OtBu)-OH | 1.0 mmol |
| 7) | Fmoc-L-Ala-OH | 1.0 mmol |
| 8) | Fmoc-L-Glu(OtBu)-OH | 1.0 mmol |
| 9) | Fmoc-L-Ser(tBu)-OH | 1.0 mmol |
| 10) | Fmoc-L-Val-OH | 1.0 mmol |
| 11) | Fmoc-L-Asn(Trt)-OH | 1.0 mmol |
| 12) | Fmoc-L-Asp(OBzl)-OH | 1.0 mmol |

The abbreviations used in identifying the above Fmoc-side chain-protected amino acids are the same as in Example 1.

Figure 5:
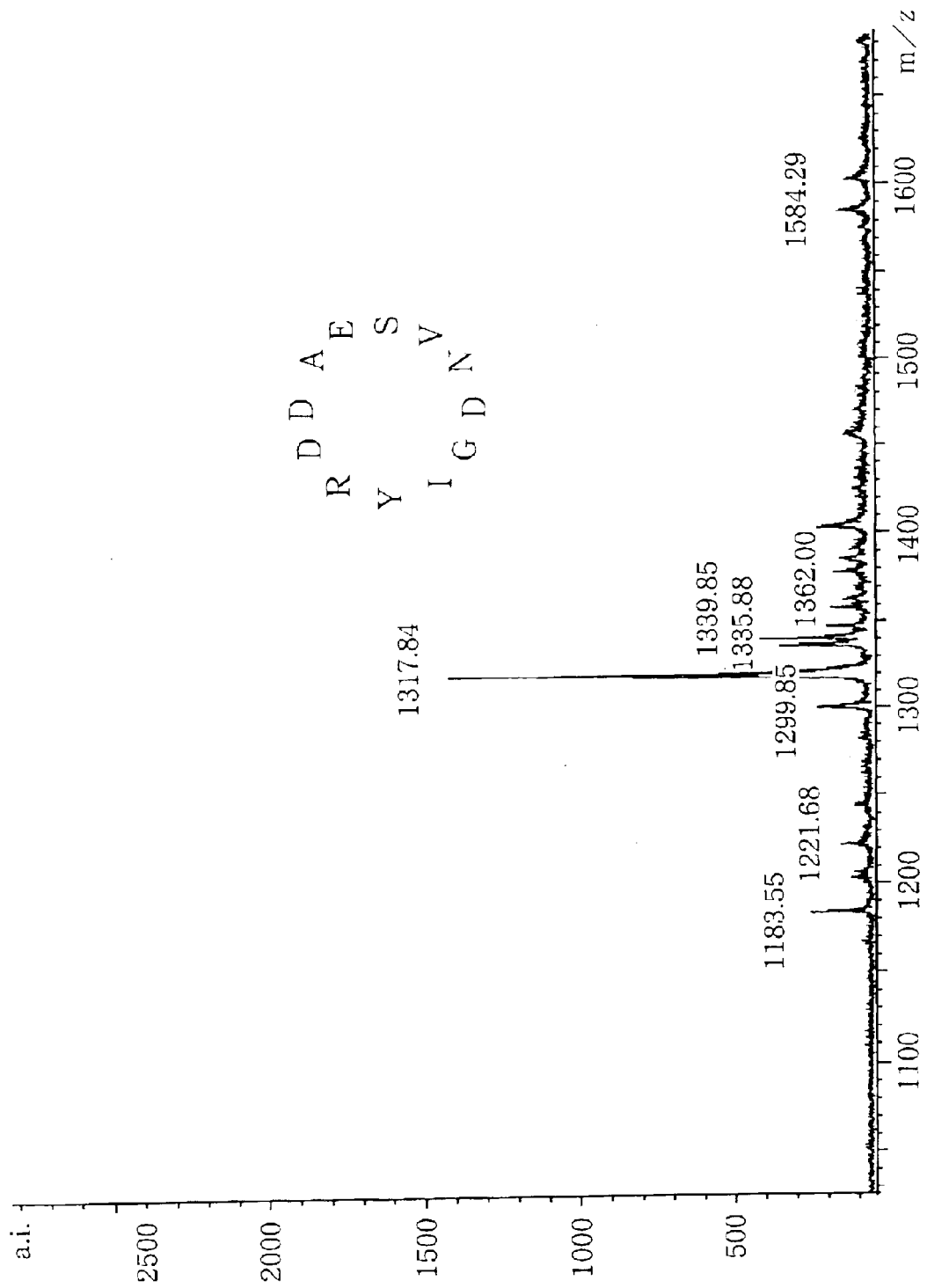
FIG. 5 shows the MALDI TOF mass spectrum for the CXCR4 cyclic dodecapeptide (CXCR4-UPL-CDDP) represented by the formula (1) (SEQ ID NO: 2).

Using the Fmoc-side chain-protected peptide resin obtained, the carboxymethyl side chain-blocked CXCR4 cyclic dodecapeptide was obtained in the same manner as in Example 1. After elimination of all the protective groups by the conventional method, the CXCR4 cyclic dodecapeptide was identified by laser mass spectrometry (MALDI-TOF mass spectrometer). The theoretical values and the values measured by laser mass spectrometry are shown below in Table 1 for the cyclic peptide and side chain (noncyclic) peptide. The MALDI TOF mass spectra are shown in FIG. 5 for the CXCR4 cyclic dodecapeptide and linear (noncylcic) dodecapeptide. Base on this result (reduction by 18, namely the molecular mass of water, as resulting from dehydration condensation under ring formation), the CXCR4 cyclic dodecapeptide (abbr.: CXCR4-UPL-CDDP) represented by the formula (1) given above was identified.

EXAMPLE 3

Synthesis of the CCR5 Cyclic Dodecapeptide

A Fmoc-side chain protected peptide resin was obtained by starting the synthesis from the C terminus on a fully automated peptide synthesizer following the same procedure as in Example 1 using the following Fmoc-side chain-protected amino acids 1) to 12) (1.0 mmol each).

| | | |
|---|---|---|
| 1) | Fmoc-Gly-OH | 1.0 mmol |
| 2) | Fmoc-L-Thr(tBu)-OH | 1.0 mmol |
| 3) | Fmoc-L-Tyr(tBu)-OH | 1.0 mmol |
| 4) | Fmoc-L-His(Trt)-OH | 1.0 mmol |
| 5) | Fmoc-L-Leu-OH | 1.0 mmol |
| 6) | Fmoc-Gly-OH | 1.0 mmol |
| 7) | Fmoc-L-Glu(OtBt)-OH | 1.0 mmol |
| 8) | Fmoc-L-Lys(Boc)-OH | 1.0 mmol |
| 9) | Fmoc-L-Gln(Trt)-OH | 1.0 mmol |
| 10) | Fmoc-L-Ser(tBu)-OH | 1.0 mmol |
| 11) | Fmoc-L-Arg(Pmc)-OH | 1.0 mmol |
| 12) | Fmoc-L-Asp(OBzl)-OH | 1.0 mmol |

The abbreviations used in identifying the above Fmoc-side chain-protected amino acids are the same as in Example 1.

Figure 6:
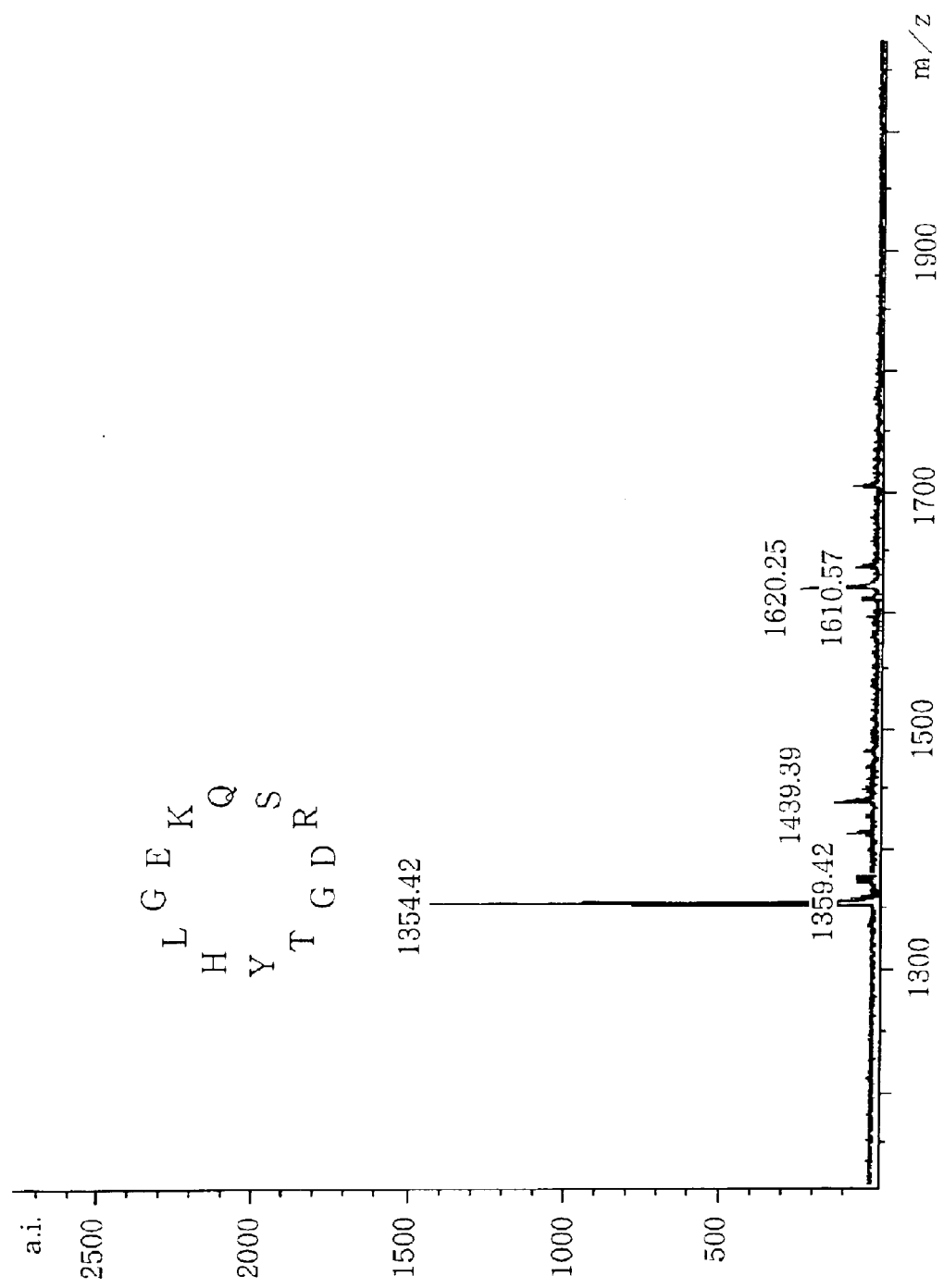
FIG. 6 shows the MALDI TOF mass spectrum for the CCR5 cyclic dodecapeptide (CCR5-UPL-CDDP) represented by the formula (2) (SEQ ID NO: 3).

Using the Fmoc-side chain-protected peptide resin obtained, the carboxymethyl side chain-blocked CCR5 cyclic dodecapeptide was obtained in the same manner as in Example 1. After elimination of all the protective groups by the conventional method, the CCR5 cyclic dodecapeptide was identified by laser mass spectrometry (MALDI-TOF mass spectrometer. The MALDI TOF mass spectra are shown in FIG. 6 for the CCR5 cyclic dodecapeptide and linear (noncylcic) dodecapeptide. Based on this result (reduction by 18, namely the molecular mass of water, as resulting from dehydration condensation under ring formation), the CCR5 cyclic dodecapeptide (abbr. CCR5-UPL-CDDP) represented by the formula (2) given above was identified.

TABLE 1

| | | Mass | Theoretical value [M + H]+ | Measured value [M + H]+ |
|---|---|---|---|---|
| Cyclic chimera peptide | Cyclic peptide | 1287.53 | 1288.53 | 1288.54 |
| | Linear (noncylcic) peptide | 1305.54 | 1306.55 | 1306.73 |
| CXCR4 cyclic dodecapeptide | Cyclic peptide | 1334.57 | 1335.57 | 1317.84[1] |
| | Linear (noncylcic) peptide | 1352.58 | 1353.59 | 1335.15[2] |
| CCR5 cyclic dodecapeptide | Cyclic peptide | 1371.65 | 1372.65 | 1354.42[3] |
| | Linear (noncylcic) peptide | 1389.66 | 1390.67 | 1372.34[4] |

The measured values 1), 2), 3) and 4) obtained by MALDI-TOF MS are smaller by 18 ($H_2O$) than the theoretical values due to intramolecular dehydration of the Asp-Gly sequence occurring in the respective sample amino acid sequences.

EXAMPLE 4

Using, as an antibody, the monoclonal antibody (CPMAb) against the CXCR4-CCR5 cyclic chimera dodecapeptide (abbr.: CXCR4-CCR5-CCDDP) obtained in Example 1 as an antigen, the immunological reactivities of CXCR4-CCR5-CCDDP (Example 1), CXCR4-CDDP (Example 2) and CCR5-CDDP (Example 3) as antigens were measured in the following manner.

The monoclonal antibody was diluted to the dilution factors shown below in Table 2 by serial two-fold dilution of the culture fluid of the hybridoma cells producing the antibody. The antigens were bound to the PIN resin to give antigens CXCR4-CCR5-CCDDP-PIN, CXCR4-CDDP-PIN and CCR5-CDDP-PIN.

96-well plates and each antigen-bound PIN resin were masked by the conventional method. Serially double-diluted antibody solutions (150 μl) were placed in the wells, the antigen-PIN resins were immersed therein, and the antigen-antibody reaction was allowed to proceed at room temperature for 60 minutes. After washing, a secondary antibody was added to each well, and the enzyme activity bound to the secondary antibody was measured. The immunological reactivities of these antigens were expressed in terms of percentage with the case of the monoclonal antibody and the corresponding antigen (CXCR4-CCR5-CCDDP) being taken as 100%. The results obtained are shown below in Table 2.

TABLE 2

| | Relative immunological reactivities | | |
|---|---|---|---|
| | Antigen | | |
| Amount of cyclic peptide/PIN | CXCR4-CCR5-CCDDP-PIN (6.5 nmol) | CXCR4-UPL-CDDP-PIN (5.5 nmol) | CCR5-UPL-CDDP-PIN (3.2 nmol) |
| Dilution factor | | 6.5/5.5 = 1.18 | 6.5/3.2 = 2.03 |
| 8 | 0.231 (100) | 0.290, 0.342 (148) | 0.157, 0.334 (145) |
| 16 | 0.172 (74) | 0.233, 0.275 (119) | 0.101, 0.205 (89) |
| 32 | 0.110 (48) | 0.152, 0.179 (77) | 0.069, 0.128 (55) |
| 64 | 0.074 (32) | 0.116, 0.137 (59) | 0.046, 0.093 (40) |
| 128 | 0.047 (20) | 0.102, 0.127 (55) | 0.046, 0.093 (40) |

According to Table 2, these three antigens have activity as antigens against the monoclonal antibody (CPMAb). In particular, the antigens obtained in Example 2 and Example 3 are high in activity, indicating that they can serve as vaccines for preventing HIV-1 infection.

Indstrial Applicability

The cyclic peptide of the present invention which comprises, as a constituent chain or chains, one or two amino acid sequences selected from among the amino acid sequence Asn-Val-Ser-Glu-Ala-Asp-Asp-Arg-Tyr-Ile (SEQ ID NO: 4) and the amino acid sequence Arg-Ser-Gln-Lys-Glu-Gly-Len-His-Tyr-Thr (SEQ ID NO: 5), more specifically, the CXCR4 cyclic dodecapeptide or CCR5 cyclic dodecapeptide represented by the above formula (1) or (2), respectively, is a novel compound.

The novel cyclic dodecapeptide of the invention is useful as an antigen for producing, in vivo, a neutralizing antibody (antibody having an anti-HIV-1 virus activity) capable of neutralizing the HIV-1 virus infection via the second receptor called CXCR4 and/or CCR5. It is also useful as an active ingredient of an AIDS vaccine.

What is claimed is:

1. An isolated cyclic peptide comprising the following formula:

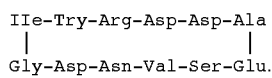

(SEQ ID NO: 2)

2. A cyclic peptide as claimed in claim 1 further comprising a substitutent group, wherein the substitutent group is bonded to at least one active group contained in the cyclic peptide, wherein the active group is selected from the group consisting of carboxyl, amino and hydroxyl.

3. A cyclic peptide as claimed in claim 2, wherein the substitutent group is selected from the group consisting of fatty acids of the formula $CH_3(CH_2)_n$—COOH, wherein n is 0 to 20; and alcohols of the formula $CH_3(CH_2)_n$—OH, wherein n is 0–20.

* * * * *

UNITED STATES PATENT AND TRADEMARK OFFICE
CERTIFICATE OF CORRECTION

PATENT NO. : 6,943,233 B1
DATED : September 13, 2005
INVENTOR(S) : Shozo Shoji

It is certified that error appears in the above-identified patent and that said Letters Patent is hereby corrected as shown below:

<u>Title page,</u>
Item [56], References Cited, FOREIGN PATENT DOCUMENTS,
"Dorang" should read -- Doranz --.

<u>Column 13,</u>
Lines 28-30, the formula:
"
```
IIe - Try - Arg - Asp - Asp - Ala
 |                             |
Gly - Asp - Asn - Val - Ser - Glu
```
" should read --
```
Ile - Try - Arg - Asp - Asp - Ala
 |                             |
Gly - Asp - Asn - Val - Ser - Glu
```
--.

Signed and Sealed this

Thirtieth Day of May, 2006

JON W. DUDAS
*Director of the United States Patent and Trademark Office*